(12) United States Patent
Wu et al.

(10) Patent No.: US 10,219,711 B2
(45) Date of Patent: Mar. 5, 2019

(54) CIRCUITS AND METHODS FOR PHOTOPLETHYSMOGRAPHIC SENSORS

(71) Applicant: Fitbit, Inc., San Francisco, CA (US)

(72) Inventors: Anjian Wu, San Francisco, CA (US); Peter W. Richards, San Francisco, CA (US); Shelten Gee Jao Yuen, Berkeley, CA (US)

(73) Assignee: Fitbit, Inc., San Francisco, CA (US)

( * ) Notice: Subject to any disclaimer, the term of this patent is extended or adjusted under 35 U.S.C. 154(b) by 0 days.

(21) Appl. No.: 15/223,589

(22) Filed: Jul. 29, 2016

(65) Prior Publication Data

US 2018/0028077 A1    Feb. 1, 2018

(51) Int. Cl.

| | |
|---|---|
| A61B 5/1455 | (2006.01) |
| A61B 5/026 | (2006.01) |
| A61B 5/024 | (2006.01) |
| A61B 5/0295 | (2006.01) |
| A61B 5/00 | (2006.01) |
| A61B 5/0255 | (2006.01) |

(52) U.S. Cl.
CPC .......... *A61B 5/0261* (2013.01); *A61B 5/0255* (2013.01); *A61B 5/0295* (2013.01); *A61B 5/02433* (2013.01); *A61B 5/02438* (2013.01); *A61B 5/681* (2013.01); *A61B 5/7203* (2013.01); *A61B 5/7278* (2013.01); *A61B 2562/0238* (2013.01)

(58) Field of Classification Search
CPC ... A61B 5/0205; A61B 5/0059; A61B 5/1455; A61B 5/14551; A61B 5/14552; A61B 5/72; A61B 5/7203; A61B 5/2562
See application file for complete search history.

(56) References Cited

U.S. PATENT DOCUMENTS

| 4,913,150 A | 4/1990 | Cheung et al. |
| 5,735,799 A | 4/1998 | Baba et al. |
| 5,830,137 A * | 11/1998 | Scharf ................ A61B 5/14552 600/323 |

(Continued)

OTHER PUBLICATIONS

U.S. Notice of Allowance, dated Apr. 12, 2017, in U.S. Appl. No. 15/223,678.

(Continued)

*Primary Examiner* — Eric Winakur
*Assistant Examiner* — Chu Chuan (JJ) Liu
(74) *Attorney, Agent, or Firm* — Weaver Austin Villeneuve & Sampson LLP

(57) ABSTRACT

Some embodiments relate to a device, method, and/or computer-readable medium storing processor-executable process steps for processing a photoplethysmographic ("PPG") signal in a monitoring device that monitors a property of blood flow. In some embodiments, the processing includes obtaining a first digital signal representing a detected light signal having a non-pulsatile (e.g., DC) component and a pulsatile component (e.g., AC). An offset control signal is generated from an estimation of the non-pulsatile component and a second digital signal is generated after subtracting the offset control signal from the detected light signal and applying a gain to the subtracted signal. A reconstructed signal is generated that is calculated from the gain and one or more of (i) the first digital signal, and (ii) the second digital signal and the offset control signal.

29 Claims, 8 Drawing Sheets

(56) References Cited

U.S. PATENT DOCUMENTS

| | | | |
|---|---|---|---|
| 5,995,858 A | 11/1999 | Kinast | |
| 8,092,393 B1 * | 1/2012 | Rulkov | A61B 5/7296 600/301 |
| 8,346,327 B2 * | 1/2013 | Campbell | A61B 5/14551 600/310 |
| 8,948,832 B2 | 2/2015 | Hong et al. | |
| 9,730,644 B1 | 8/2017 | Wu et al. | |
| 2003/0073890 A1 | 4/2003 | Hanna | |
| 2009/0281402 A1 * | 11/2009 | Chance | A61B 5/0059 600/328 |
| 2010/0292548 A1 | 11/2010 | Baker et al. | |
| 2010/0331638 A1 | 12/2010 | Besko | |
| 2014/0107493 A1 * | 4/2014 | Yuen | A61B 5/02416 600/473 |
| 2015/0031971 A1 * | 1/2015 | Lisogurski | A61B 5/14552 600/324 |
| 2015/0335293 A1 * | 11/2015 | Christman | A61B 5/14551 600/324 |

OTHER PUBLICATIONS

U.S. Office Action, dated Nov. 30, 2016, in U.S. Appl. No. 15/223,678.

* cited by examiner

CIRCUITS AND METHODS FOR PHOTOPLETHYSMOGRAPHIC SENSORS

BACKGROUND

Field

The embodiments described below relate to the measurement of biometric data. Some embodiments relate to photoplethysmographic sensors.

Description

Recent consumer interest in personal health has led to a variety of personal health monitoring devices being offered on the market. Such devices, until recently, tended to be complicated to use and were typically designed for use with one activity, e.g., bicycle trip computers.

Recently, personal health monitoring devices (also referred to herein as "biometric tracking" or "biometric monitoring" devices) have expanded to track multiple metrics of the wearer. For example, Fitbit, Inc. produces a number of biometric tracking devices that can have a number of features and elements, such as displays, batteries, sensors, wireless communications capabilities, power sources, and interface buttons, as well as mechanisms for attaching these devices to a pocket or other portion of clothing or to a body part of the wearer, packaged within a small volume which are configured to track, among other things, steps, distance, calorie expenditure, active minutes, elevation (e.g., as measured in floors or stairs), speed, pace, and the like.

To track these metrics, these devices may collect, process and display a large variety of data using a variety of sensors. One type of sensor used in some biometric tracking devices is a heart rate sensor. These heart rate sensors typically operate by emitting light into the skin of the user and then measuring the light reflected or diffused back after the emitted light interacts with the user's skin.

SUMMARY

Some embodiments relate to a device, method, and/or computer-readable medium storing processor-executable process steps for processing a photoplethysmographic ("PPG") signal in a monitoring device that monitors a property of blood flow. In some embodiments, the processing includes obtaining a first digital signal representing a detected light signal having a non-pulsatile (e.g., DC) component and a pulsatile component (e.g., AC). An offset control signal is generated from an estimation of the non-pulsatile component and a second digital signal is generated after subtracting the offset control signal from the detected light signal and applying a gain to the subtracted signal. A reconstructed signal is generated that is calculated from the gain and one or more of (i) the first digital signal, and (ii) the second digital signal and the offset control signal.

In some embodiments, generation of the offset control signal includes selecting a value for the offset control signal such that the second digital signal, which is generated after the offset control signal is subtracted from the first digital signal and adjusted by the gain, does not exceed a range threshold. The offset control signal may be generated by selecting an initial value, determining that the first digital signal subtracted by the offset control signal and then adjusted by the gain does not exceed a range threshold, selecting a subsequent value for the offset control signal, and determining that the first digital signal adjusted by the subsequent value of the offset control signal and gain does not exceed the range threshold.

In some embodiments, the monitoring device may include multiple light emitters to generate a source light signal. A control unit associated with the monitoring device may switch between the light emitters to generate the source light signal. The multiple light emitters may include emitters that emit the source light in different wavelength regions (e.g., such as red, green and infrared regions).

In some embodiments, a monitoring device may be provide which supports two modes of operation to measure different properties of a blood flow. For example, in some embodiments, the device may allow measurement of both heart rate and blood oxygenation levels. In some embodiments, a method for processing a photoplethysmographic (PPG) signal in a monitoring device includes receiving a signal selecting a mode of operation of the monitoring device. A switching component is operated to select a first light source in a first mode of operation and a second light source in a second mode of operation. A selected one of the first and the second light sources are operated to generate a source light signal. A first digital representation of the detected light signal is obtained, and a second digital signal is generated based at least in part on the selected mode of operation. The second digital signal is provided to a processor for use in measuring a property of blood flow. In some embodiments, the first mode of operation is a mode to measure a heart rate and a second mode of operation is a mode to measure a blood oxygenation level. In some embodiments, when a first mode of operation is selected, an offset control component is disabled, and when a second mode of operation is selected, the offset control component is enabled to allow subtraction of a DC component of the detected light signal.

Embodiments as described herein provide a number of advantages. For example, embodiments provide monitoring devices with reduced cost which can efficiently extract and resolve the pulsatile component of a PPG signal allowing improved processing of PPG signals. In some cases, embodiments provide such improved processing without use of high resolution analog-to-digital ("ADC") converters or oversampling techniques which can be expensive and consume additional power. Further, embodiments allow faster processing and signal acquisition time.

A more complete understanding of some embodiments can be obtained by referring to the following detailed description and to the drawings appended hereto.

BRIEF DESCRIPTION OF THE DRAWINGS

The construction and usage of embodiments will become readily apparent from consideration of the following specification as illustrated in the accompanying drawings, in which like reference numerals designate like parts, and wherein.

DETAILED DESCRIPTION

The following description is provided to enable any person in the art to make and use the described embodiments. Various modifications, however, will remain readily apparent to those in the art. A specific example will now be described with reference to the appended figures in order to provide an introduction to various features. Embodiments are not limited to the features or description of this example.

Figure 1:
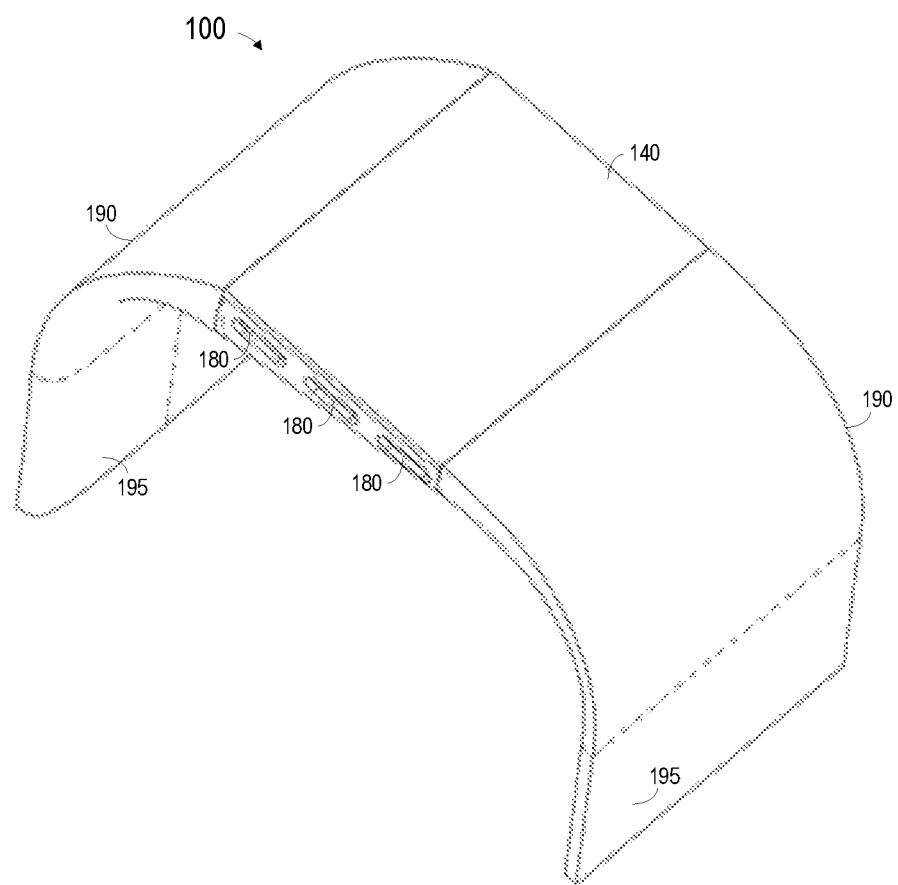
FIG. 1 is a top perspective view of a device according to some embodiments.

As discussed above, monitoring devices utilizing the methods and/or circuitry discussed herein can be used to collect and monitor biometric information. An example of such a monitoring device 100 is shown in FIG. 1. According to the illustrated embodiment, the device 100 is wearable on a user's wrist. The device 100 includes a display 140, which may comprise any suitable type of display screen, and which may display graphical indicators based on biometric and other data detected, collected, monitored or otherwise generated by the device 100. The device 100 may include one or more buttons 180 which may be manipulated by a user to provide input to the device 100. The display 140 may also incorporate one or more input devices (such as a touch screen). A band 190 may be wrapped around the wrist and is securable using one or more securing elements 195 (e.g., hook and loop, clasp, shape memory elements, magnets). The shape and configuration of the device 100 is one example configuration within which embodiments of the present invention may be deployed. The monitoring devices and PPG sensor system and methods set forth herein may be used with desirable results in devices having a wide variety of shapes and configurations, and the shape and configuration illustrated in FIG. 1 and FIG. 2 are for illustrative purposes.

Figure 2:
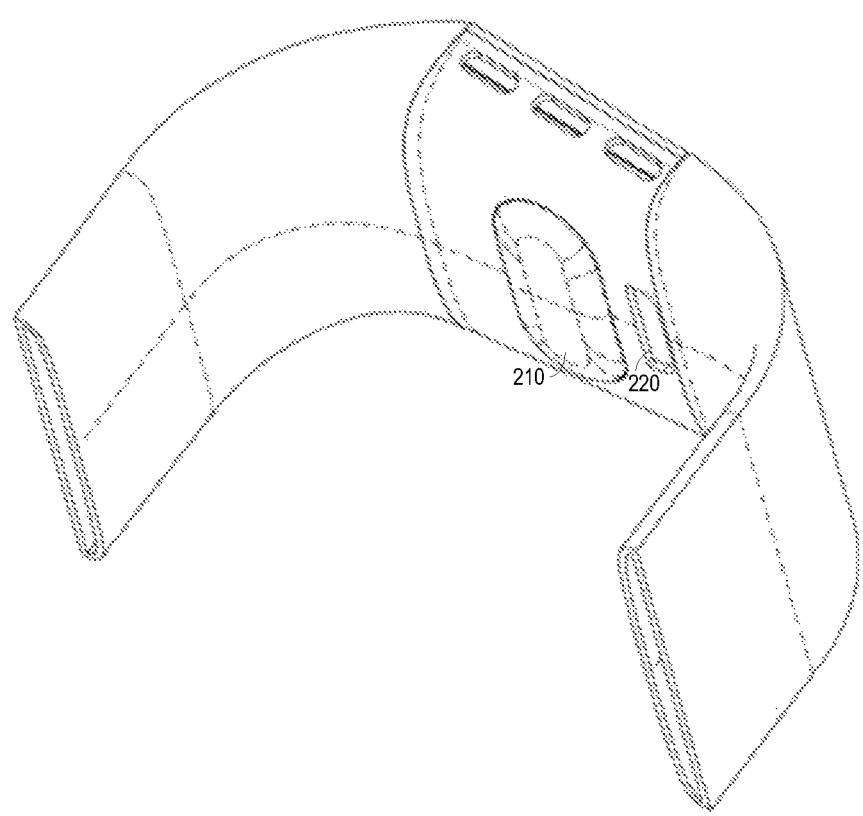
FIG. 2 is a bottom perspective view of a device according to some embodiments.

FIG. 2 is a bottom view of the device 100, showing a sensor component 210 and a power interface 220. The sensor component 210 may include sensors which benefit from close proximity and/or contact with a user's skin tissue. Such sensors may include PPG sensors (e.g., heart rate, pulse oximeter, and the like), moisture, temperature, and/or capacitive touch sensors (e.g., to detect when the device is being worn). The power interface 220 may interface with a docking station or other power source to receive electrical charge for charging of batteries located within the device 100. Although a single sensor component 210 is shown for simplicity, multiple sensor components may be provided. Further, while the sensor component 210 is illustrated in FIG. 2 as protruding somewhat from the device 100, other embodiments may place sensors in proximity to the user without use of a distinct protrusion.

Features of a particular category or type of sensor—a "PPG" or "photoplethysmographic" sensor—will be described in further detail herein. PPG sensors, such as a heart rate monitor or pulse oximeter, use a light-based technology to sense pulsating blood flow as controlled by the heart's pumping action. PPG sensors may be used to measure a user's heart rate, blood oxygenation, and other biometric parameters. In the device 100 shown in FIG. 1 and FIG. 2, sensor component 210 may shield or be associated with one or more light sources (e.g., such as photodiodes, light emitting diodes or "LEDs") and light detector(s) and corresponding control circuitry (e.g., as described further below). In some cases, light pipes may be used to optically connect the light source(s) or the detector with the surface of the user's skin tissue. Beneath the skin, the light from the light sources scatters off of blood in the body, some of which may be scattered or reflected back into a photodetector located behind the sensor component 210. In some embodiments, as will be described further herein, the sensor component 210 may be shaped and formed to improve the operation of the sensor. For example, in some embodiments, the sensor component 210 may utilize light-transmissive structures to improve the performance of a PPG sensor. For example, a light-transmissive structure may include a mask consisting of an opaque material that limits the aperture of one, some or all of the light source(s) and/or detector(s). In this way, the light-transmissive structures may selectively define or control a preferential volume of the user's body that light is emitted into and/or detected from.

Figure 3:
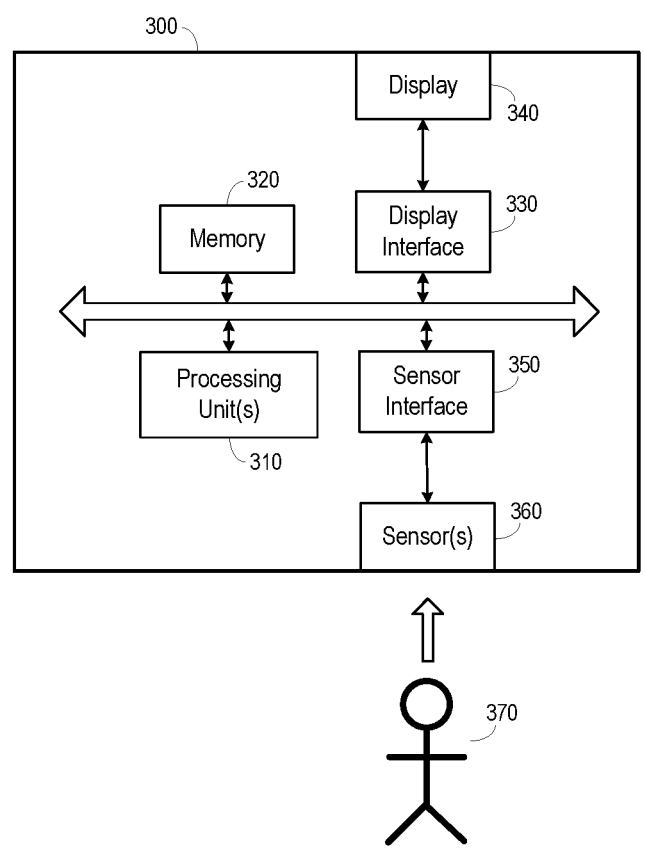
FIG. 3 is a block diagram of a device according to some embodiments.

FIG. 3 is a block diagram of a monitoring system 300 according to some embodiments. System 300 may be operated to control the collection and usage of biometric data pursuant to some embodiments. In some cases, the monitoring system 300 may implement internal features of the device 100 shown in FIGS. 1 and 2.

As FIG. 3 shows, the system 300 includes one or more processing units 310 (e.g., hardware elements, such as processor cores and/or processing threads, discrete or integrated logic, and/or one or more state machines, and/or field programmable gate arrays (or combinations thereof)). In some cases, one or more processing units 310 are configured to execute processor-executable program code to cause the device 300 to operate as described herein, and memory 320 for storing the program code and any other suitable data. The memory 320 may comprise one or more fixed disks, solid-state random access memory, and/or removable media (e.g., a thumb drive) mounted in a corresponding interface (e.g., a USB port).

A display interface 330 provides communication with the display 340, which may comprise any system for visual presentation of information that is or becomes known. The display 340 may comprise a touch screen for receiving user input into the system 300 according to some embodiments. The display 140 shown in FIG. 1 is an example of the display 340.

One or more processing units 310 may execute processor-executable program code stored in memory 320 to cause the system 300 to process sensor data control the operation of sensors and related components, and to perform operations as discussed herein. In some embodiments, the processing unit 310 may be configured as a processor core, memory and programmable input and output peripherals and may be referred to herein as a microcontroller (or "MCU"). According to some embodiments, the system 300 comprises an integrated device such as, but not limited to, a wearable unit (e.g., around a user's wrist such as the device 100 shown in FIGS. 1 and 2, around the user's neck, attached to an earlobe or inserted in an ear (e.g., an earbud), on a ring, or the like) or an otherwise portable unit (e.g., a smartphone, a dedicated music player, a fob). In some embodiments, elements of the system 300 may be embodied in separate devices, such as a server device (e.g., a desktop computer) including elements 310, 320 and 330, and a terminal device (e.g., a watch) including the display 340. The system 300 may perform functions other than those attributed thereto herein, and may include any elements that are necessary for the operation thereof.

Some embodiments of the system 300 include a portable monitoring device having a physical size and shape adapted to couple to the body of a user, which allows the user to perform normal or typical user activities (including, for example, exercise of all kinds and type) without hindering the user from performing such activities. An example of such a device is the device 100 of FIG. 1. The portable monitoring device may include a mechanism (for example, a clip, strap and/or tie) that facilitates coupling or affixing the device to the user during such normal or typical user activities.

The system 300 further includes one or more sensor interfaces 350 for exchanging data with one or more sensors 360. The sensors 360 may comprise any sensors for acquiring data including biometric monitoring data. Examples of sensors 360 include, but are not limited to, an accelerometer, a light sensor, a compass, a switch, a pedometer, a blood oxygen sensor, a gyroscope, a magnetometer, a Global Positioning System device, a proximity sensor, a pressure sensor (e.g., an altimeter), and a heart rate sensor. One or more of the sensors 360 may share common hardware and/or software components.

As shown in FIG. 3, a user 370 is pictured to indicate that, according to some embodiments, the user 370 influences the data acquired by one or more of the one or more sensors 360. For example, the one or more sensors 360 may generate data based on physical activity of the user 370. Moreover, one or more of sensors 360 may generate data via direct contact with the user, for example during heart rate, skin temperature, and/or blood oxygen monitoring.

Figure 4:
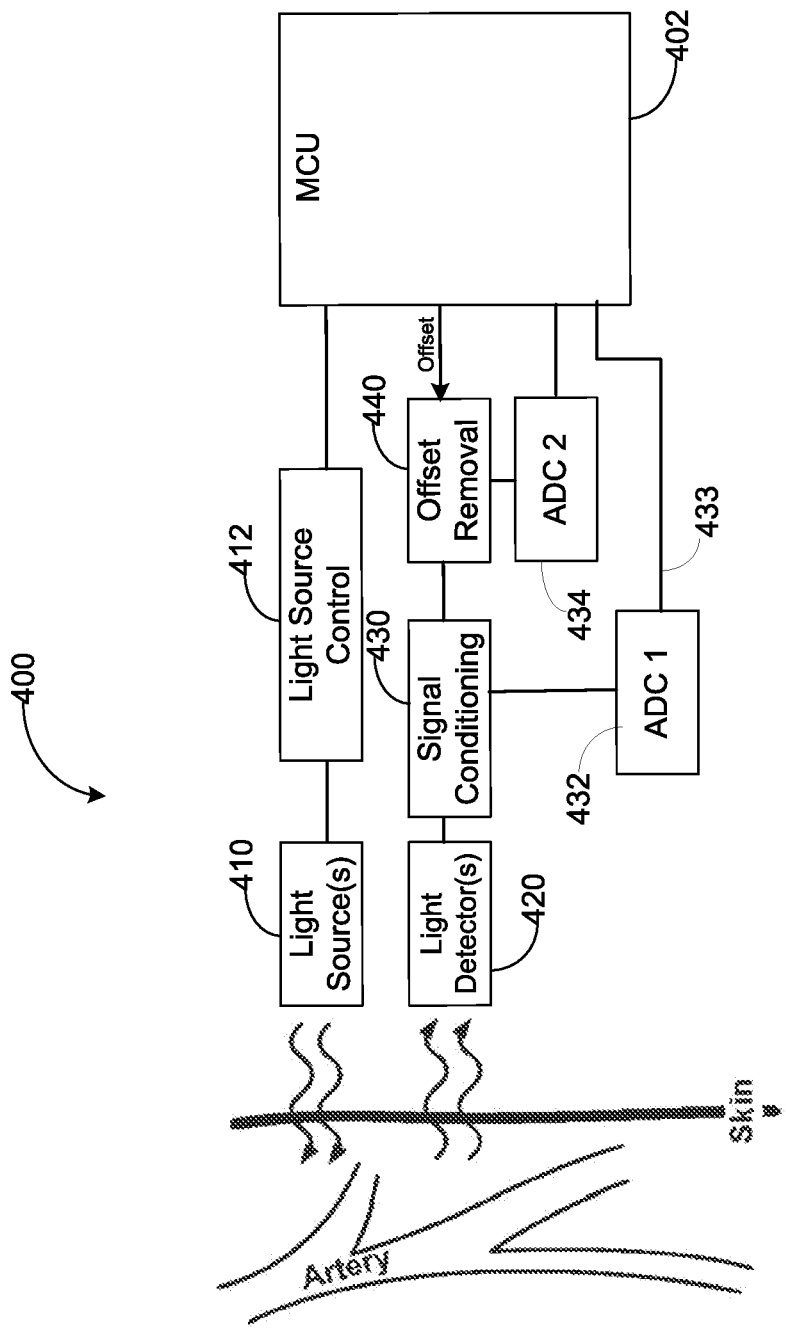
FIG. 4 is a block diagram of a sensor pursuant to some embodiments.

Reference is now made to FIG. 4, where an example block diagram of a sensor 400 is shown which may be used as one of multiple sensors 360 of the device 300 in FIG. 3. As will be described further below, embodiments of the sensor 400 may be operated or configured to function as both an optical heart rate sensor and a blood oxygenation sensor. As shown in FIG. 4, the sensor 400 includes one or more light sources 410 which emit light toward a user's skin tissue, and where the reflection and/or diffusion of such light from the skin/internal tissues of the user is sensed by one or more light detectors 420, the signal from which is subsequently digitized by one or more analog to digital converters ("ADC") 432, 434 (referred to as "ADC 1" and "ADC 2", respectively).

In general, a PPG signal is an optically and non-invasively obtained signal used to sense volumic changes of blood vessels. A light source 410 emits at the tissue of interest (e.g., the skin shown in FIG. 4) and a light detector 420 is placed to measure the transmitted or reflected light. Depending on the wavelengths of the light source 410, information about a person such as heart rate and blood oxygenation can be determined.

The light sources 410 may be, for example, one or more photodiodes which are configured to generate a light in a wavelength. For example, a photodiode may be provided as a light source 410 and configured to generate light in the red, infrared, or green regions (660 nm, 940 nm, and 528 nm, respectively). As will be described further herein, the sensor 400 may be configured with one or more light sources 410 operating in the infrared and red wavelengths for use in obtaining blood oxygen measurements (e.g., operating as an SpO2 sensor). One or more additional light sources 410 may be provided which operate in the green wavelength region for use as a heart rate sensor.

Embodiments of the present invention allow the sensor 400 to be operated in different modes of operation depending on whether the infrared/red wavelengths or the green wavelengths are used. For example, the sensor may be operated in a mode to discern information about a user's heart rate (when the green wavelength light sources 410 are operated) and in a mode to discern information about a user's blood oxygenation (when the infrared and red wavelength light sources 410 are operated). In general, both the infrared and red PPG signals' pulsatile components are much weaker in comparison to that of the green wavelength signals and are more susceptible to uncertainty due to noise. In the infrared and red wavelengths, there is a large offset component of the PPG signal (referred to herein as the "non-pulsatile" or "DC" component) and the pulsatile component (also referred to herein as the "AC" component). For example, the AC component of the detected PPG signal can be as small as 0.05% of the signal, leaving up to 99.95% of the dynamic range unusable. Put another way, in a sensor using 12-bit resolution ADCs, the best effective resolution of the AC component of the PPG signal may be less than 2-bits. The use of very high-resolution ADCs to enable higher effective resolution of the AC component is undesirable in many sensor systems, particularly where power, cost and size are important.

In order to obtain accurate signal information for a processor (such as the processor 310 of FIG. 3) or microcontroller (shown as MCU 402) to perform processing of the detected signals, the light information detected by the light detectors 420 is processed using a front-end signal conditioning block 430 which directly interfaces with the light detectors 420 and which outputs an analog PPG signal. This PPG signal is provided to an ADC 432 which is configured with sufficient resolution to measure the non-pulsatile (DC) component of the PPG signal (but maybe not enough resolution for the pulsatile or AC component). This digital signal 433 (which may be referred to elsewhere herein as the "first digital signal") is provided to the MCU 402 for processing. Upon receipt of the first digital Signal 433, the MCU 402 performs processing to generate an offset signal (as will be described further herein). The offset signal is provided from the MCU 402 to an offset removal stage 440. The offset removal stage 440 receives the offset signal from the MCU 402 and removes the offset value from the signal 530. The MCU 402 calculates what value the offset signal should be and provides it to the offset removal stage 440 to remove the value of the offset signal from the signal from ADC 432. In general, the offset removal stage 440 provides a modified PPG signal representing primarily the pulsatile (or AC) component of the PPG signal to a second ADC 434 for digitization and for provision to the MCU 402 for use in processing to determine a detected blood oxygenation level. In some embodiments, the MCU 402 includes memory which stores control and application data as well as signal data. In some embodiments, the MCU 402 stores data such as the digital signal 433, offset signal data and the signal received from ADC 434 in a memory as time series data. For example, the signal data may be stored such that the MCU 402 may reconstruct a PPG signal as described further below in conjunction with FIGS. 7 and 8.

As discussed above, pursuant to some embodiments, multiple light sources 410 may be provided (e.g., including light sources for different wavelengths). The operation and selection of different light sources (as well as the intensity of the selected light source 410) may be controlled using one or more light source controls 412. The light source controls 412 may be operated by control signals received from the MCU 402. For example, in some embodiments, a light source 410 may be controlled to enable the light source 410 (and, in some embodiments, to set a desired intensity) based on a mode of operation selected by the MCU 402. As one illustrative example, a mode of operation may be a mode in which an optical heart rate is to be detected. In such a mode, one or more light sources 410 capable of generating light in a green wavelength region may be operated. As another illustrative example, a mode of operation may be a mode in which a blood oxygenation measurement is to be taken. In such a mode, one or more light sources 410 capable of generating light in an infrared wavelength region may be operated as well as one or more light sources 410 capable of generating light in a red wavelength region. In some embodiments, the MCU 402 may be operated to switch between different light sources 410 and/or different light detectors 420 based on a desired mode of operation.

The light source control module 412 may be controlled by the MCU 402. The MCU 402 receives digital signals from one or both of the ADCs 432, 434 and may use that information to generate control signals including the offset control signal as well as control signals to operate the light source control 412 and light sources 410. The MCU 402 may adaptively control the operation of the light source 412 based on operating information received from the first and/or second ADCs (432, 434), allowing a wide variety of operating controls. Further, in some embodiments, the MCU 402 may control whether the second ADC 434 is operated based on the mode of operation (e.g., in some embodiments, the second ADC 434 is not operated when the sensor is in a mode of operation to obtain an optical heart rate measurement).

Figure 5:
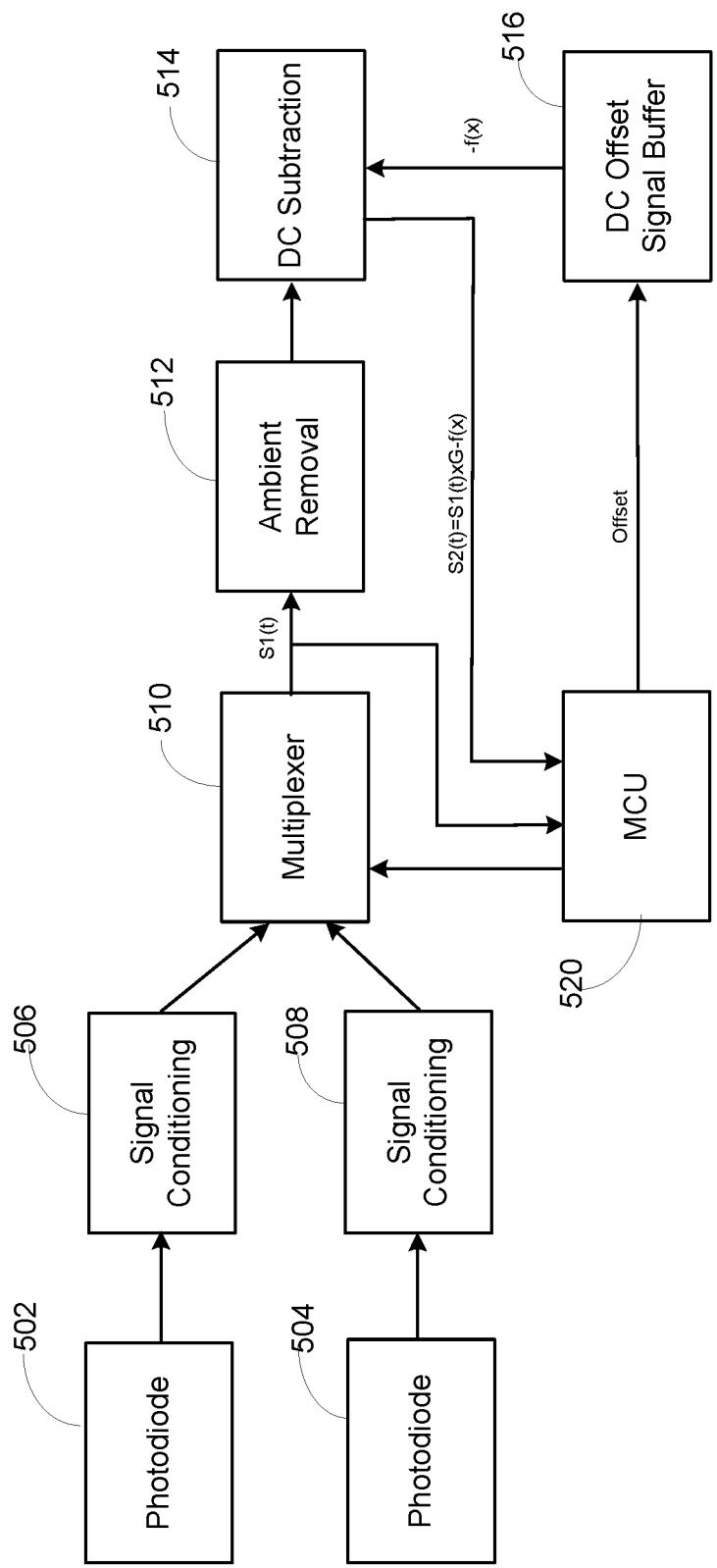
FIG. 5 is a block diagram of components of a sensor pursuant to some embodiments.

Features of some embodiments will now be described in further detail by reference to FIG. 5, which is a block diagram depicting components of the sensor device of FIG. 4 in further detail. More particularly, FIG. 5 depicts the logical blocks and functions that allow the generation of signals for provision to the MCU 520 for further processing of blood oxygenation analysis and heart rate analysis. As shown in FIG. 5, a sensor device may be provided with a number of components, including one or more photodiodes 502, 504 and one or more signal conditioning components 506, 508 which correspond to the photodiodes. While two sets of photodiodes 502, 504 and signal conditioning components 506, 508 are shown, sensors may be provided with more than two sets as will be described further herein. The sensor further includes or is in communication with an MCU 520 that performs processing to control components of the sensor and to perform processing of signals generated by the sensor. For example, the MCU 520 may generate control signals to operate a multiplexor 510 which allows control over which photodiode 502, 504 to use as the signal source. For example, the MCU 520 may issue control signals to select photodiode 502 and signal conditioning block 506 as the source signal.

As a more specific illustrative example, the MCU 520 may generate the control signal based on a mode of operation selected by a user of the monitoring device (e.g., the user may select to operate the monitoring device to capture an optical heart rate measurement, or the user may select to operate the monitoring device to capture a blood oxygen measurement). For example, the photodiode 502 may be a photodiode that operates in a green wavelength region, and the photodiode 502 (and associated signal conditioning component 506) may be enabled by a control signal from the MCU 520 which selects that signal source through the multiplexor 510. In the following discussion, an embodiment will be described in which the photodiode 502 is a green wavelength photodiode, and the photodiode 504 is a set of photodiodes that operate in the infrared and red wavelengths and are used for SpO2 measurements.

Figure 6:
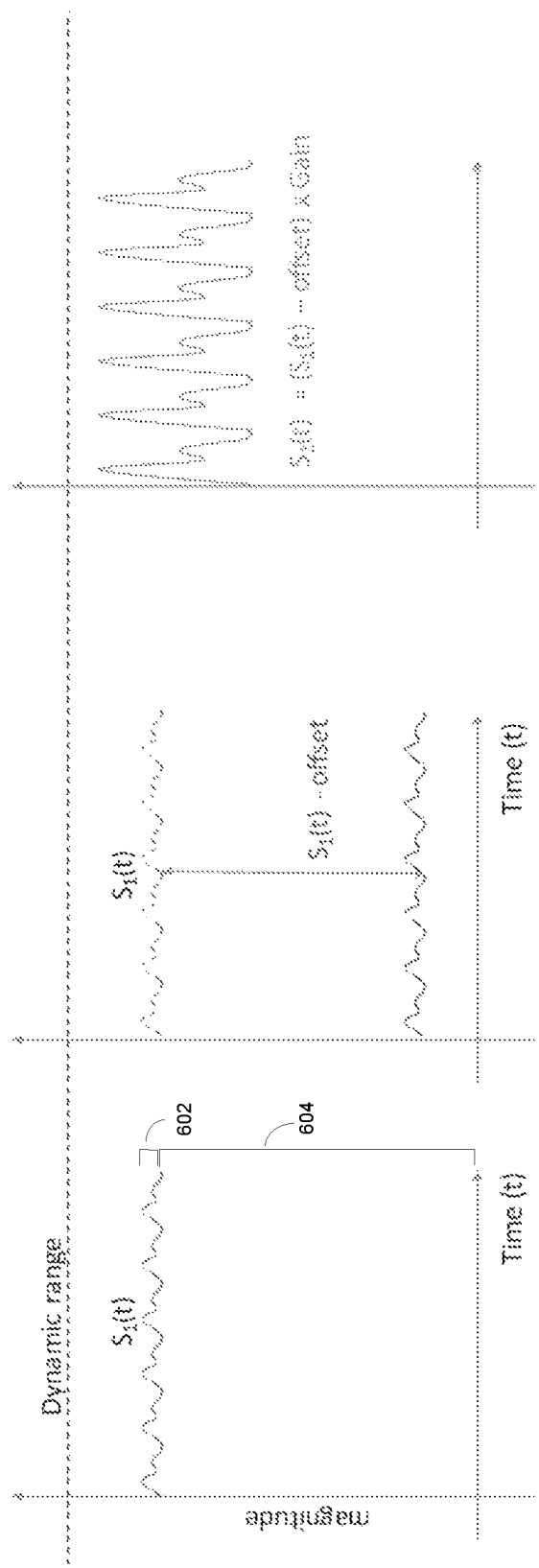
FIGS. 6A-6C are diagrams illustrating a photoplethysmographic ("PPG") signal as processed by the device of FIGS. 4 and 5 pursuant to some embodiments.

Once the MCU 520 has selected a PPG signal source (e.g., photodiode 502 or photodiode 504), the multiplexor 510 may pass the PPG signal from the selected signal source to an ambient removal component 512. The PPG signal is shown on FIG. 5 as signal $S1(t)$. The signal $S1(t)$ is also provided as an input to the MCU 520 and is used for further processing as described below. The PPG signal $S1(t)$ is processed by an ADC (such as the stage one ADC 432 of FIG. 4). In general, the input to the MCU 520 is a digital representation of the PPG signal $S1(t)$ that represents the PPG signal (including both the AC and the DC components of the signal) at a point in time. A sample illustration of the PPG signal $S1(t)$ is shown in FIG. 6A, where the magnitude of the PPG signal is shown over time. As shown, the signal has a relatively small amount of information (shown as region 602) with a large offset (shown as region 604).

In some embodiments, the PPG signal $S1(t)$ may further be processed using an ambient removal component 512 which operates to remove an ambient component of the signal (although this processing is optional and will not be described in detail herein).

The MCU 520, having received the digital representation of the PPG signal $S1(t)$, performs processing to generate an offset signal. The offset signal may be selected or determined by the MCU 520 based on a predetermined value selected such that the gain times the result of the signal $S1(t)$ less the offset value is within the dynamic range of the ADCs of the sensor. The offset value may be dynamically updated as $S1(t)$ is received by the MCU 520. In some embodiments, the offset value may be selected such that the adjusted signal is above a predetermined or calculated minimum, but also below a maximum (such that the signal $S1(t)$ is within the dynamic range of the ADCs of the sensor). Referring to FIG. 6B, a sample illustration of the signal $S1(t)$ less the offset signal is shown. The offset signal is provided as an input to a DC offset signal buffer 516 for provision to a DC subtraction component 514. The DC offset signal buffer 516 may include a digital to analog converter ("DAC") to generate the appropriate offset voltage level based on the offset signal from the MCU 520. The DC subtraction component 514 generates a second PPG signal $S2(t)$ which is generally equivalent to a gain times the result of the first signal ($S1(t)$) less the DC offset. Put another way, the output of the DC subtraction component 514 is generally equivalent to the AC component of the PPG signal with some DC left. A representation of the signal $S2(t)$ is shown in FIG. 6C. In general, the offset (illustrated in FIG. 6B) is selected to allow the gain (applied in FIG. 6C) to be applied while staying within the dynamic range of the system. The result is a signal $S2(t)$ that has a larger AC component. The signal $S2(t)$ is provided to a second ADC (such as the ADC 434 of FIG. 4) to generate a digital representation of the signal $S2(t)$ for provision to the MCU 520.

Figure 7:
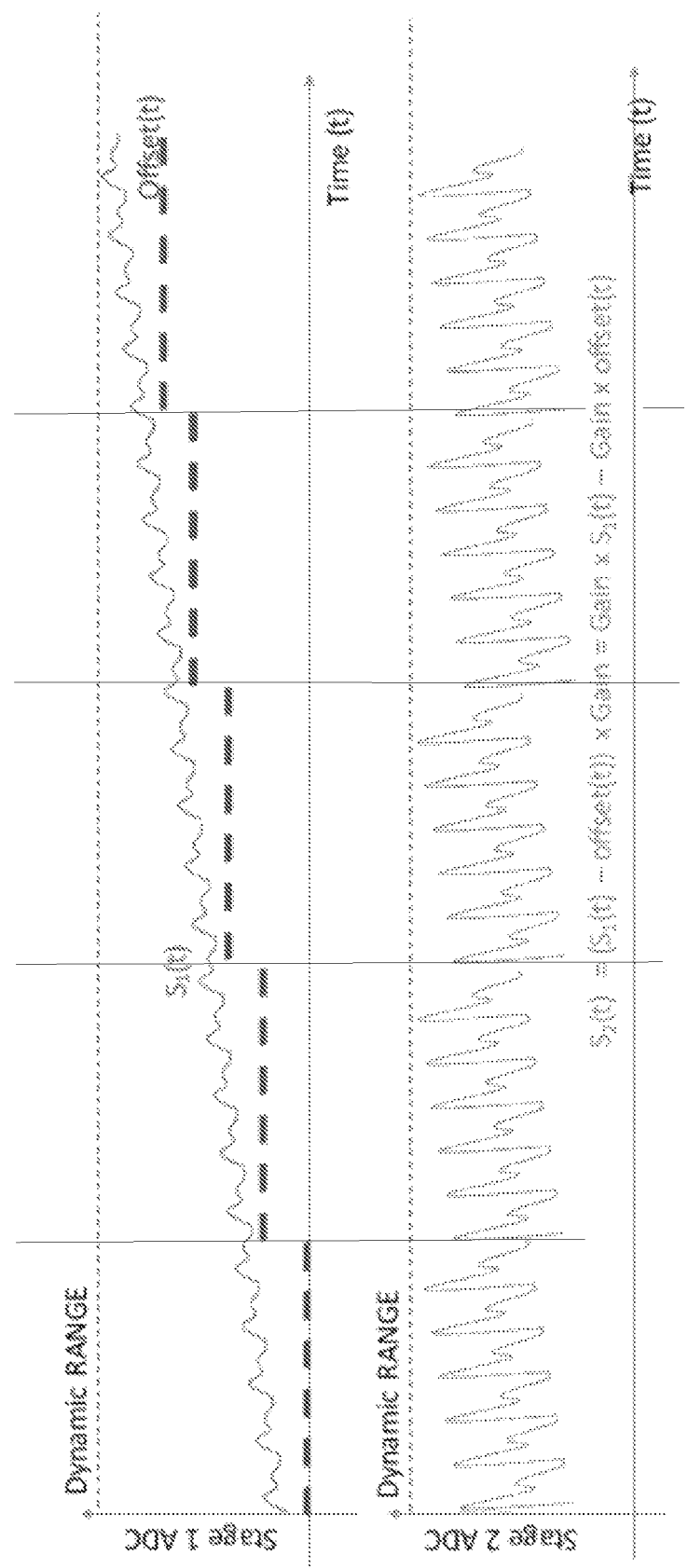
FIG. 7 is a diagram illustrating a PPG signal as processed by the device of FIGS. 4 and 5 pursuant to some embodiments.
Figure 8:
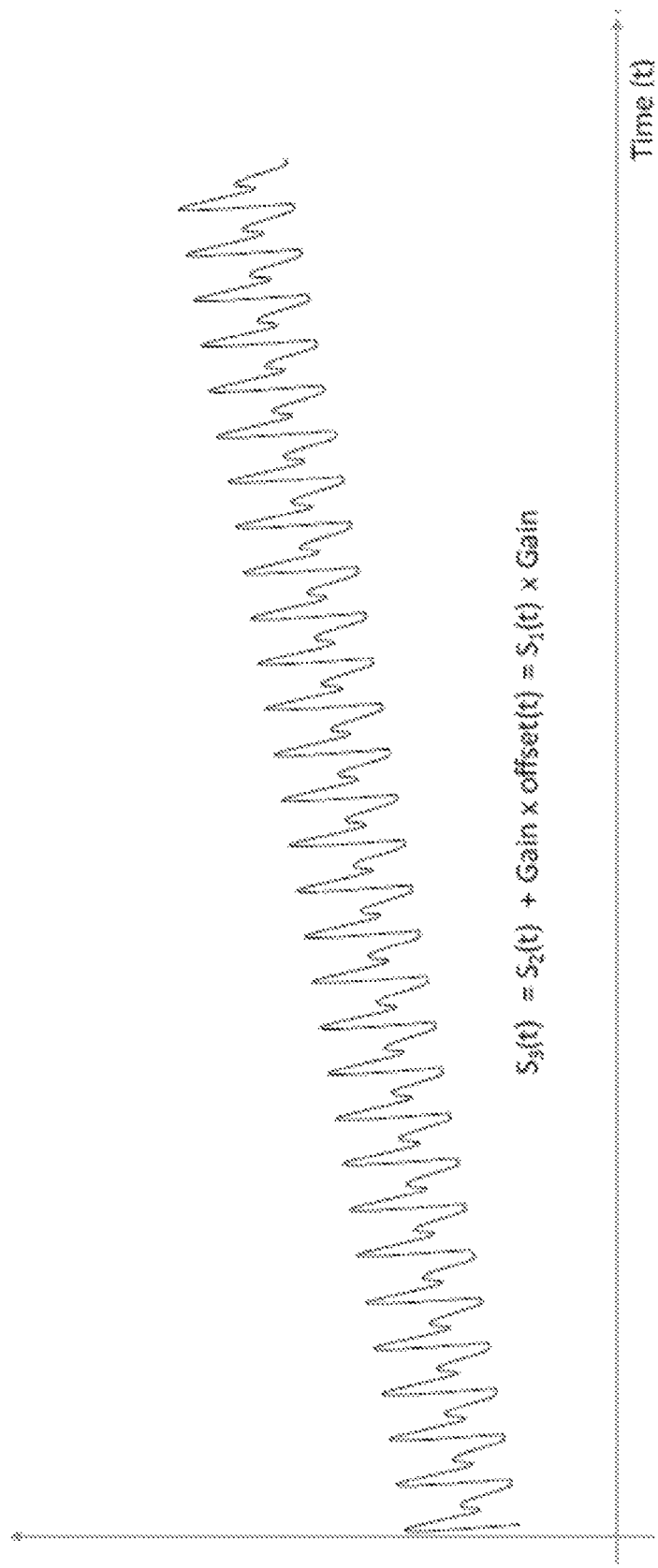
FIG. 8 is a diagram illustrating a reconstructed PPG signal pursuant to some embodiments.

Reference is now made to FIG. 7, where a representation of the PPG signals as processed by the MCU 520 over time are shown. In the top portion of FIG. 7, the signal $S1(t)$ over time is shown. As shown, the offset determined by the MCU 520 may vary over time, but is selected such that the signal $S2(t)$ does not extend beyond the dynamic range of the ADCs of the system. The MCU 520 stores the signal information for $S1(t)$, $S2(t)$, the gain, and the offset(t), and this signal information is associated with a time period for which it is relevant. The different time periods (with the offset values shown in the stage 1 ADC chart) are illustrated with vertical lines separating each time period. The MCU 520 may then perform processing to reconstruct the PPG signal. Referring to FIG. 8, the MCU 520 may perform processing to construct a PPG signal S3(t) which may be calculated from S1(t), S2(t), the gain, and the offset(t). In general, S3(t) is equivalent to S1(t) multiplied by the gain, or S2(t) plus the gain multiplied by the offset(t). The resulting signal (S3(t)) allows the MCU 520 to perform processing on a signal with more resolution and without need for expensive high-resolution ADCs or oversampling to resolve the AC component of the PPG signal. In this manner, embodiments provide more resolution for PPG signals because the DC component of the PPG signal can be subtracted before amplification.

Further, embodiments allow a monitoring device to be operated with different types of biometric measurements. For example, devices consistent with the embodiments shown in FIGS. 4 and 5 may be operated to obtain measurements for both heart rate (which may use photodiodes operating in the green wavelength) as well as SpO2 (which may use photodiodes operating in the red and infrared wavelengths). Pursuant to some embodiments, the DC subtraction component 514 operates independently of which mode of operation is used. In some embodiments, when the device is operated in a mode to obtain heart rate measurements, a photodiode 502 operating in the green wavelength is enabled (or selected as the PPG signal source by the multiplexor 510) and the offset control signal is set to equal zero. When the device is operated in a mode to obtain SpO2 measurements, photodiodes 504 operating in the red and infrared wavelengths are enabled (or selected as the PPG signal source by the multiplexor 510) and the offset control signal is determined as described above. Further, depending on the selected mode of operation, the MCU 520 may be enabled to reconstruct a signal S3(t) (as shown in FIG. 8) or the signal reconstruction may be disabled. For example, when the device is operated in a SpO2 measurement mode of operation the offset control signal is determined as described above and the MCU 520 is configured to perform a signal reconstruction. When the device is operated in a heart rate measurement mode of operation, the offset control signal is set to zero and the MCU 520 is configured to not perform a signal reconstruction. In this manner, embodiments allow multiple modes of operation using the same components, without expensive high-resolution ADCs to resolve the AC component of signals (particularly for SpO2 modes of operation).

The foregoing diagrams represent logical architectures for describing processes according to some embodiments, and actual implementations may include more or different components arranged in other manners. Other topologies may be used in conjunction with other embodiments. Moreover, each system described herein may be implemented by any number of devices in communication via any number of other public and/or private networks. Two or more of such computing devices may be located remote from one another and may communicate with one another via any known manner of network(s) and/or a dedicated connection. Each device may include any number of hardware and/or software elements suitable to provide the functions described herein as well as any other functions. For example, any computing device used in an implementation of some embodiments may include a processor to execute program code such that the computing device operates as described herein.

The modules and components described herein may be implemented in hardware, a processor executing firmware and/or software instructions, or any combination thereof. For instance, memory portions of processing modules may be implemented in one or more memory devices such as one or more of a magnetic disk, an optical disk, a random access memory (RAM), a video RAM, a Flash memory, etc. Similarly, processing units of processing or control modules (such as, for example, the light source control module 412 of FIG. 4) may be implemented using one or more of discrete components, an integrated circuit, an application-specific integrated circuit (ASIC), a programmable logic device (PLD), etc. If the module, processor and/or processing units are implemented using a processor executing firmware and/or software instructions, the software or firmware instructions may be stored in any computer readable memory such as on a magnetic disk, an optical disk, in a RAM or ROM or Flash memory, a memory of a processor (e.g., a cache memory), etc. The processor executing firmware and/or software instructions may comprise a general purpose processor or a special purpose processor such as a digital signal processor (DSP), a graphics processor, or the like.

Those in the art will appreciate that various adaptations and modifications of the above-described embodiments can be configured without departing from the scope and spirit of the claims. Therefore, it is to be understood that the claims may be practiced other than as specifically described herein.

What is claimed is:

1. A method for processing a photoplethysmographic (PPG) signal in a monitoring device that measures a property of blood flow, the method comprising:

causing one or more first light sources to emit light in the green wavelength spectrum during first periods of time;

causing one or more second light sources to collectively emit light in the red and infrared wavelength spectra during second periods of time different from the first periods of time;

obtaining a detected light signal from one or more detectors during the first and second periods of time, the detected light signal including pulsatile and non-pulsatile components;

obtaining a first digital signal representing the detected light signal;

generating, from the first digital signal, an offset control signal from an estimation of the non-pulsatile component; generating a second digital signal by subtracting the offset control signal from the detected light signal to produce a subtracted signal and then applying a gain to the subtracted signal;

generating a reconstructed signal calculated from the gain, the second digital signal, and the offset control signal;

setting the offset control signal to zero while generating the reconstructed signal for each first period of time;

outputting data derived from portions of the reconstructed signal associated with the first periods of time as a heart rate; and outputting data derived from portions of the reconstructed signal associated with the second periods of time as a blood oxygenation level.

2. The method of claim 1, wherein generating the offset control signal includes:

selecting a value for the offset control signal such that the second digital signal does not exceed a range threshold.

3. The method of claim 2, wherein generating the offset control signal includes:

selecting an initial value for the offset control signal;

determining that the second digital signal exceeds a range threshold;

selecting a subsequent value for the offset control signal; and determining that the second digital signal does not exceed the range threshold.

4. The method of claim 1, further comprising:

constructing a digital representation over time of the detected light signal based on the data derived from the reconstructed signals.

5. The method of claim 4, wherein one or more of the second periods of time are consecutive and at least one of the offset control signals and the gains used to generate the reconstructed signal for the one or more consecutive second periods of time varies from one second period of time to the next second period of time.

6. The method of claim 1, wherein the first digital signal is generated by an analog-to-digital converter with sufficient resolution to measure, during the second periods of time, the non-pulsatile component but not the pulsatile component.

7. The method of claim 1, wherein the detected light signal represents the light emitted by the one or more first light sources or the one or more second light sources after interacting with a skin tissue, wherein the method further comprises:

operating a switching component to switch between the one or more first light sources and the one or more second light sources.

8. The method of claim 1, further comprising:

generating the detected light signal using one or more first photodetectors during the first periods of time, generating the detected light signal using one or more second photodetectors during the second periods of time, and operating a switching component to switch between the one or more first photodetectors and the one or more second photodetectors.

9. The method of claim 1, wherein the one or more first light sources are configured to emit light in a wavelength region of approximately 528 nm.

10. The method of claim 1, wherein the one or more second light sources are collectively configured to emit light in wavelength regions of approximately 660 nm and approximately 940 nm.

11. The method of claim 1, wherein:

the one or more first light sources are configured to emit light in a wavelength region of approximately 528 nm, the one or more second light sources are collectively configured to emit light in wavelength regions of approximately 660 nm and approximately 940 nm.

12. The method of claim 7, wherein the operating the switching component to switch between the one or more first light sources and the one or more second light sources is based on a selected mode of operation of the monitoring device.

13. The method of claim 1, further comprising:

removing, from the first digital signal and prior to generating the second digital signal, a signal corresponding to a component of the detected light signal that is not the result of operation of the one or more first light sources or the one or more second light sources.

14. The method of claim 1, further comprising storing one or more of the first digital signal, the offset control signal, and the second digital signal in a memory in a time series data set.

15. The method of claim 8, further comprising:

operating an emitter switching component to switch between the one or more first light sources and the one or more second light sources.

16. A photoplethysmographic monitoring device, comprising:

one or more first light sources configured to emit light in the green wavelength spectrum;

one or more second light sources configured to collectively emit light in the red and infrared wavelength spectra;

one or more detectors;

one or more processors; and a non-transitory, computer-readable medium storing instructions which, when executed, cause the one or more processors to:

cause one or more first light sources to emit light in the green wavelength spectrum during first periods of time;

cause one or more second light sources to collectively emit light in the red and infrared wavelength spectra during second periods of time different from the first periods of time;

cause a detected light signal to be obtained from one or more detectors during the first and second periods of time, the detected light signal including pulsatile and non-pulsatile components;

cause a first digital signal representing the detected light signal to be obtained;

cause an offset control signal to be generated from an estimation of the non-pulsatile component in the first digital signal;

cause a second digital signal to be generated by subtracting the offset control signal from the first digital signal to produce a subtracted signal and then applying a gain to the subtracted signal;

cause a reconstructed signal to be calculated from the gain, the second digital signal, and the offset control signal;

cause the offset control signal to be set to zero while generating the reconstructed signal for each first period of time;

cause data derived from portions of the reconstructed signal associated with the first periods of time to be output as a heart rate; and cause data derived from portions of the reconstructed signal associated with the second periods of time to be output as a blood oxygenation level.

17. The photoplethysmographic monitoring device of claim 16, wherein the non-transitory computer-readable medium stores further instructions which, when executed, cause the one or more processors to:

operate a switch component to switch between the one or more first light sources and the one or more second light sources.

18. The photoplethysmographic monitoring device of claim 16, wherein the one or more detectors includes one or more first photodetectors and one or more second photodetectors and wherein the non-transitory computer-readable medium stores further instructions which, when executed, cause the one or more processors to:

generate the detected light signal using one or more first photodetectors during the first periods of time, and generate the detected light signal using one or more second photodetectors during the second periods of time.

19. The photoplethysmographic monitoring device of claim 16, wherein the one or more first light sources are configured to emit light in a wavelength region of approximately 528 nm and the one or more second light sources, collectively, are configured to emit light in a second wavelength region of approximately 660 nm and a third wavelength region of approximately 940 nm.

20. The photoplethysmographic monitoring device of claim 16, wherein the non-transitory computer-readable medium stores further instructions which, when executed, cause the one or more processors to generate the offset control signal by selecting a value for the offset control signal such that the second digital signal does not exceed a range threshold.

21. The photoplethysmographic monitoring device of claim 20, wherein the non-transitory computer-readable medium stores further instructions which, when executed, cause the one or more processors to:
   select an initial value for the offset control signal;
   determine that the second digital signal exceeds a range threshold;
   select a subsequent value for the offset control signal; and
   determine that the second digital signal does not exceed the range threshold.

22. The photoplethysmographic monitoring device of claim 16, wherein the non-transitory computer-readable medium stores further instructions which, when executed, cause the one or more processors to:
   construct a digital representation over time of the detected light signal based on the data derived from the reconstructed signals.

23. The photoplethysmographic monitoring device of claim 22, wherein one or more of the second periods of time are consecutive and at least one of the offset control signals and the gains used to generate the reconstructed signal for the one or more consecutive second periods of time varies from one second period of time to the next second period of time.

24. The photoplethysmographic monitoring device of claim 16, further comprising an analog-to-digital converter with sufficient resolution to measure, during the second periods of time, the non-pulsatile component but not the pulsatile component, wherein the analog-to-digital converter is configured to generate the first digital signal.

25. A non-transitory computer-readable medium storing computer-executable instructions for processing a photoplethysmographic signal in a monitoring device that measures a property of a blood flow, the computer-executable instructions, when executed, causing one or more processors to:
   cause one or more first light sources to emit light in the green wavelength spectrum during first periods of time;
   cause one or more second light sources to collectively emit light in the red and infrared wavelength spectra during second periods of time different from the first periods of time;
   cause a detected light signal to be obtained from one or more detectors during the first and second periods of time, the detected light signal including pulsatile and non-pulsatile components;
   cause a first digital signal representing the detected light signal to be obtained;
   cause an offset control signal to be generated from an estimation of the non-pulsatile component in the first digital signal;
   cause a second digital signal to be generated by subtracting the offset control signal from the first digital signal to produce a subtracted signal and then applying a gain to the subtracted signal;
   cause a reconstructed signal to be calculated from the gain, the second digital signal, and the offset control signal;
   cause the offset control signal to be set to zero while generating the reconstructed signal for each first period of time;
   cause data derived from portions of the reconstructed signal associated with the first periods of time to be output as a heart rate; and
   cause data derived from portions of the reconstructed signal associated with the second periods of time to be output as a blood oxygenation level.

26. The non-transitory computer-readable medium of claim 25, further storing computer-executable instructions that, when executed, further cause the one or more processors to:
   select a value for the offset control signal such that the second digital signal does not exceed a range threshold.

27. The non-transitory computer-readable medium of claim 26, further storing computer-executable instructions that, when executed, further cause the one or more processors to:
   select an initial value for the offset control signal;
   determine that the second digital signal exceeds a range threshold;
   select a subsequent value for the offset control signal; and
   determine that the second digital signal does not exceed the range threshold.

28. The non-transitory computer-readable medium of claim 25, further storing computer-executable instructions that, when executed, further cause the one or more processors to:
   construct a digital representation over time of the detected light signal based on the data derived from the reconstructed signals.

29. The non-transitory computer-readable medium of claim 28, wherein:
   one or more of the second periods of time are consecutive and at least one of the offset control signals and the gains used to generate the reconstructed signal for the one or more consecutive second periods of time varies from one second period of time to the next second period of time.

* * * * *